(12) United States Patent
Spratt et al.

(10) Patent No.: US 11,013,546 B2
(45) Date of Patent: May 25, 2021

(54) ROD BENDER

(71) Applicant: Medos International Sarl, Le Locle (CH)

(72) Inventors: Frank Spratt, Middleboro, MA (US); Sheryl Furlan, Lakeville, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/352,378

(22) Filed: Mar. 13, 2019

(65) Prior Publication Data

US 2020/0289181 A1 Sep. 17, 2020

(51) Int. Cl.
*A61B 17/88* (2006.01)
*B21D 7/00* (2006.01)
*A61B 17/70* (2006.01)

(52) U.S. Cl.
CPC ............ *A61B 17/8863* (2013.01); *B21D 7/00* (2013.01); *A61B 17/7013* (2013.01)

(58) Field of Classification Search
CPC .. A61B 17/8863; A61B 17/8861; B21F 1/002
USPC ........................................................ 606/101
See application file for complete search history.

(56) References Cited

U.S. PATENT DOCUMENTS

| | | | | |
|---|---|---|---|---|
| 5,113,685 | A | * | 5/1992 | Asher ................ A61B 17/7007 140/106 |
| 5,161,404 | A | * | 11/1992 | Hayes .................... B21D 7/063 140/106 |
| 5,389,099 | A | | 2/1995 | Hartmeister et al. |
| 5,564,302 | A | | 10/1996 | Watrous |
| 7,131,975 | B2 | * | 11/2006 | Adams ................ A61B 17/26 606/101 |
| 7,488,331 | B2 | | 2/2009 | Abdelgany |
| 8,043,298 | B2 | | 10/2011 | Capanni |
| 8,235,998 | B2 | | 8/2012 | Miller et al. |
| 8,419,745 | B2 | | 4/2013 | Sixto et al. |
| 8,454,665 | B2 | | 6/2013 | Sidebotham |

(Continued)

FOREIGN PATENT DOCUMENTS

| | | |
|---|---|---|
| GB | 2448123 A | 10/2008 |
| WO | 2014/107144 A1 | 7/2014 |

OTHER PUBLICATIONS

International Search Report received for PCT Application No. PCT/EP2020/056321 dated Mar. 27, 2020.

*Primary Examiner* — Matthew J Lawson
(74) *Attorney, Agent, or Firm* — Mintz Levin Cohn Ferris Glovsky and Popeo, P.C.

(57) ABSTRACT

Surgical methods and devices are provided for bending spinal rods. In one embodiment, a handheld tool is provided having an elongate shaft with a lumen formed therein that is configured to accommodate a spinal rod. The tool can include an opening in a proximal end that is configured to permit the loading of the spinal rod into the lumen, and a plurality of openings spaced along a longitudinal axis thereof that intersect the lumen for allowing a user to view and/or grasp a rod extending through the rod-receiving lumen and positioned within one of the plurality of openings. The tool can further be configured to permit a bent spinal rod to be received within the lumen. For example, the tool can include a channel in a lower surface thereof that allows a rod to exit the lumen and to extend laterally away from the tool.

20 Claims, 9 Drawing Sheets

(56) References Cited

U.S. PATENT DOCUMENTS

| | | |
|---|---|---|
| 8,459,090 B2 | 6/2013 | Wilcox et al. |
| 9,585,706 B2 | 3/2017 | Prasad et al. |
| 9,956,599 B2 | 5/2018 | Tellman et al. |
| 2011/0264100 A1* | 10/2011 | Sixto, Jr. ............ A61B 17/8863 606/101 |
| 2013/0091921 A1* | 4/2013 | Wilcox ................. B21F 1/002 72/458 |
| 2013/0296954 A1 | 11/2013 | Skaggs et al. |
| 2014/0135842 A1* | 5/2014 | Wallenstein ....... A61B 17/7032 606/267 |
| 2015/0289918 A1 | 10/2015 | Burckhardt et al. |
| 2017/0281252 A1* | 10/2017 | Schwab ............. A61B 17/8863 |
| 2017/0290615 A1 | 10/2017 | Schwab et al. |
| 2017/0340373 A1 | 11/2017 | Zhang et al. |
| 2020/0214752 A1* | 7/2020 | Schwab ............. A61B 17/8863 |

* cited by examiner

ROD BENDER

FIELD

Surgical devices, systems, and methods are provided for the bending of spinal rods.

BACKGROUND

Some spinal surgeries require the use of polyaxial or monoaxial screws that are linked together by spinal rods. The rods can have a plastic yield point such that a user can use a rod bending tool to bend the rod to a desired shape prior to implantation. Current rod bending tools include a lumen for accommodating the spinal rod, allowing a user to insert the spinal rod into the lumen, and to bend portions of the rod extending from the lumen as the rod is incrementally retracted from the lumen. As such, a user cannot re-insert a bent rod into the lumen to make any adjustments to the shape as may be required during a surgical procedure.

Accordingly, there remains a need for systems, methods and devices for bending spinal rods.

SUMMARY

Surgical devices, systems, and methods are provided for the bending of spinal rods. In one embodiment, a spinal rod bending tool is provided having an elongate shaft extending along a longitudinal axis. The elongate shaft can have a substantially rectangular cross section with upper and lower surfaces. In some embodiments, the upper and lower surfaces can have a width that is greater than a height of opposed side surfaces extending between the upper and lower surfaces. The tool can further include a rod-receiving lumen extending at least partially through the elongate shaft along the longitudinal axis. The rod-receiving lumen can have a proximal opening at a proximal end of the elongate shaft that is configured to receive a spinal rod, and in some embodiments the rod-receiving lumen terminate proximal to a distal end of the elongate shaft.

The tool can also include a plurality of openings spaced along the longitudinal axis, with each opening extending entirely through the upper and lower surfaces of the elongate shaft, such that a user can grasp a rod extending through the rod-receiving lumen and positioned within one of the plurality of openings. In some embodiments, each of the plurality of openings can have a shape in the form of an isosceles trapezoid. In such an embodiment, each of the plurality of openings can, in some implementations, have a short side and a long side, wherein the plurality of openings can alternate between the short side and the long side being oriented toward a first side of the elongate shaft.

The tool can also include an extended opening formed in the lower surface of the elongate shaft adjacent to the proximal opening. The extended opening can be configured to allow a pre-bent rod inserted through the proximal opening and into the rod-receiving lumen to extend laterally away from the lower surface. In some embodiments, the extended opening can extend across and connect first and second openings of the plurality of openings.

In other embodiments, the tool can include a locking feature at the proximal end of the elongate shaft. The locking feature can be configured to engage and lock a rod extending through the rod-receiving lumen.

In other aspects, a distal portion of the elongate shaft can be oriented at a transverse angle to the longitudinal axis of the elongate shaft.

In another embodiment, a rod bender tool is provided having an elongate rectangular shaft with a proximal end and a distal end defining a longitudinal axis. The elongate rectangular shaft can have a substantially cylindrical lumen extending through the shaft from the proximal end and terminating proximal to the distal end. The elongate rectangular shaft can further include a plurality of thru-holes spaced along the longitudinal axis, and each thru-hole can intersect the substantially cylindrical lumen. The elongate rectangular shaft can also include an elongate channel formed in a lower surface of the elongate shaft and intersecting at least two of the thru-holes and the substantially cylindrical lumen. In some embodiments, the elongate rectangular shaft can have upper and lower surfaces, with the plurality of thru-holes extending through the upper and lower surfaces and the elongate channel being formed in a lower surface.

In some embodiments, each of the plurality of openings can have a shape in the form of an isosceles trapezoid. In such an embodiment, each of the plurality of openings can have a short side and a long side, wherein the plurality of openings can alternate between the short side and the long side being oriented toward a first side of the elongate shaft.

In other embodiments, the distal portion of the elongate shaft can be oriented at a transverse angle to the longitudinal axis of the elongate shaft.

In still other embodiments, the tool can include a locking feature at the proximal end of the elongate shaft. The locking feature can be configured to engage and lock a rod extending through the substantially cylindrical lumen.

In another embodiment, a method for bending a rod is provided. The method can include inserting a pre-bent spinal rod into a lumen extending longitudinally through an elongate shaft of a rod bender tool such that a leading end of the rod extends through one of a plurality of openings formed in the elongate shaft, projects from a lower surface of the elongate shaft, and extends laterally away from the longitudinal axis of the elongate shaft. The method can further include grasping and manipulating a remaining trailing end of the pre-bent spinal rod extending from a proximal end of the elongate shaft to bend the remaining trailing end.

In some embodiments, at least a portion of the pre-bent rod can extend through a channel formed in the lower surface of the elongate shaft, and the channel can be in communication with first and second openings of the plurality of openings.

In other embodiments, the method can include grasping a portion of the pre-bent spinal rod extending through one of the plurality of openings.

In still other embodiments, the method can include partially retracting the pre-bent spinal rod from the lumen, and repeating the step of grasping and manipulating a remaining trailing end of the pre-bent spinal rod extending from the proximal end of the elongate shaft to bend the remaining trailing end.

In yet other embodiments, the method can include, prior to grasping and manipulating, actuating a locking mechanism to lock the pre-bent spinal rod at a fixed position relative to the elongate shaft. In such embodiments, the method can include, after grasping and manipulating, releasing the locking mechanism by positioning the locking mechanism within one of a plurality of openings formed in a second rod bender tool, and rotating the tool to rotate the locking mechanism.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Surgical methods and devices are provided for bending spinal rods. In general, a handheld tool is provided having an elongate shaft with a lumen formed therein that is configured to accommodate a spinal rod. The tool can include an open proximal portion that is configured to permit the loading of the spinal rod into the lumen, and a plurality of channels formed therein and spaced therealong. The tool can further include an extended channel or opening formed along a lower surface thereof adjacent the proximal opening for allowing a pre-bent spinal rod to extend laterally away from the tool. Such a tool thus permits a user to manipulate and bend a spinal rod in a non-sequential fashion, which allows for increased flexibility in bending a spinal rod to suit a spinal implant site. The tool can also include a variety of other features to facilitate use thereof.

FIGS. 1-7 show one exemplary embodiment of a spinal rod bending tool 100. As shown, the tool has a generally elongate shaft 102. The elongate shaft 102 can have a variety of shapes and sizes, but in the illustrated embodiment, it has a substantially rectangular cross-sectional shape. The elongate shaft 102 thus have an upper surface 104, a lower surface 106, and a opposed side surfaces 108a, 108b extending between and joining the upper and lower surfaces 104, 106. The elongate shaft 102 can extend linearly along a longitudinal axis A for a substantial portion of its length. In certain embodiments, the elongate shaft 102 can extend linearly along its entire length, except for a distal portion 110 of the elongate shaft 102 which can be angularly oriented relative to the remainder of the shaft 102, as will be discussed in more detail below.

The elongate shaft 102 can have a variety of sizes. In the illustrated embodiment of FIGS. 1-7, the upper and lower surfaces 104, 106 have a width that is greater than a height of the opposed side surfaces 108a, 108b extending between the upper and lower surfaces to define the substantially rectangular cross-sectional shape. A proximal portion 112, however, can have a generally square cross-sectional shape, such that the proximal portion 112 has a height between the upper and lower surfaces that is greater than the height between the upper and lower surfaces 104, 106 of the remainder of the shaft 112. The length of the elongate shaft 102 extending between proximal and distal ends 102p, 102d can be sufficient to allow varying lengths of a spinal rod to be inserted therein, and to allow a user to grasp and manipulate the tool. The size can vary based on the intended use. Moreover, the elongate shaft can be manufactured from a variety of materials, such as various metals or plastics.

Figure 2:
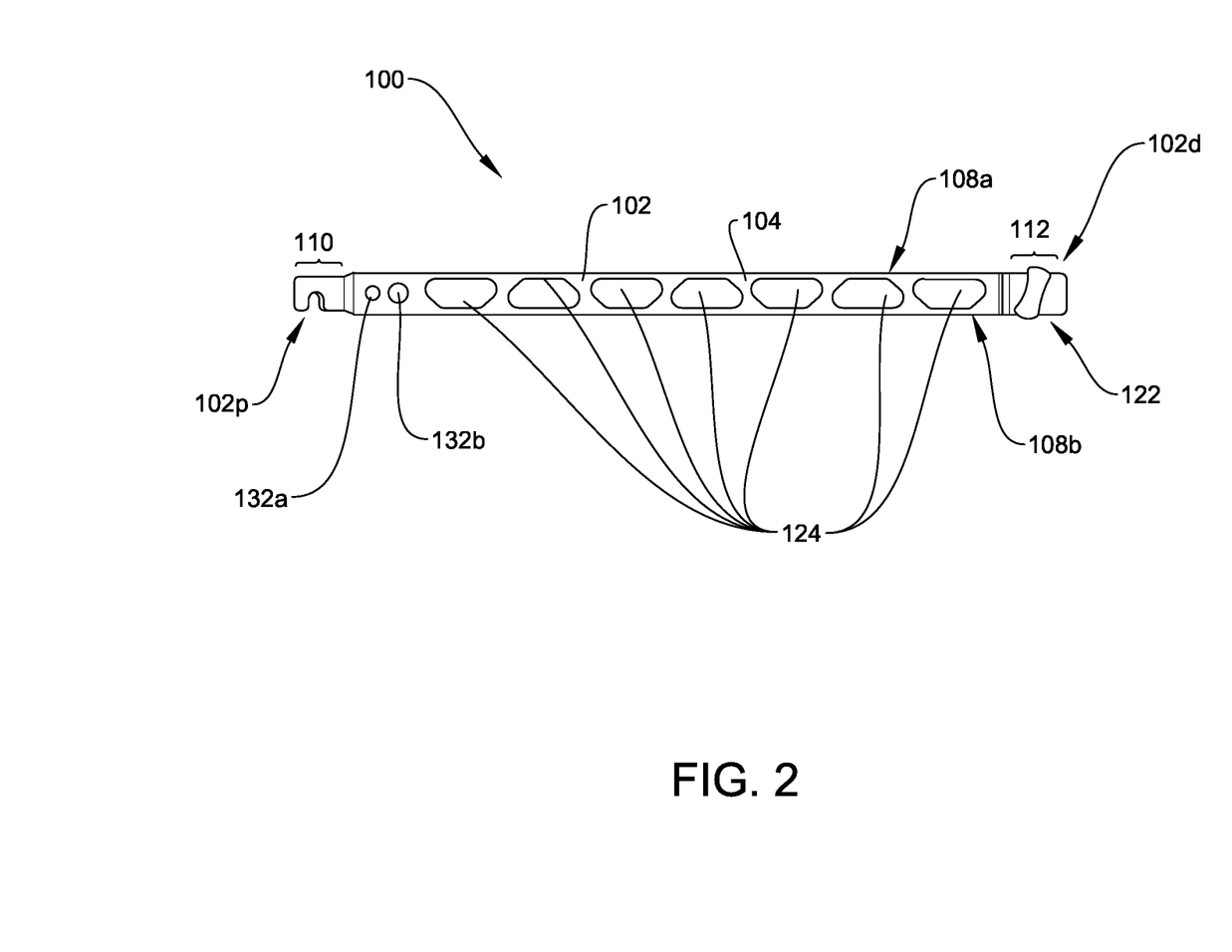
FIG. 2 is a side view of the tool of FIG. 1, with the spinal rod removed.
Figure 3:
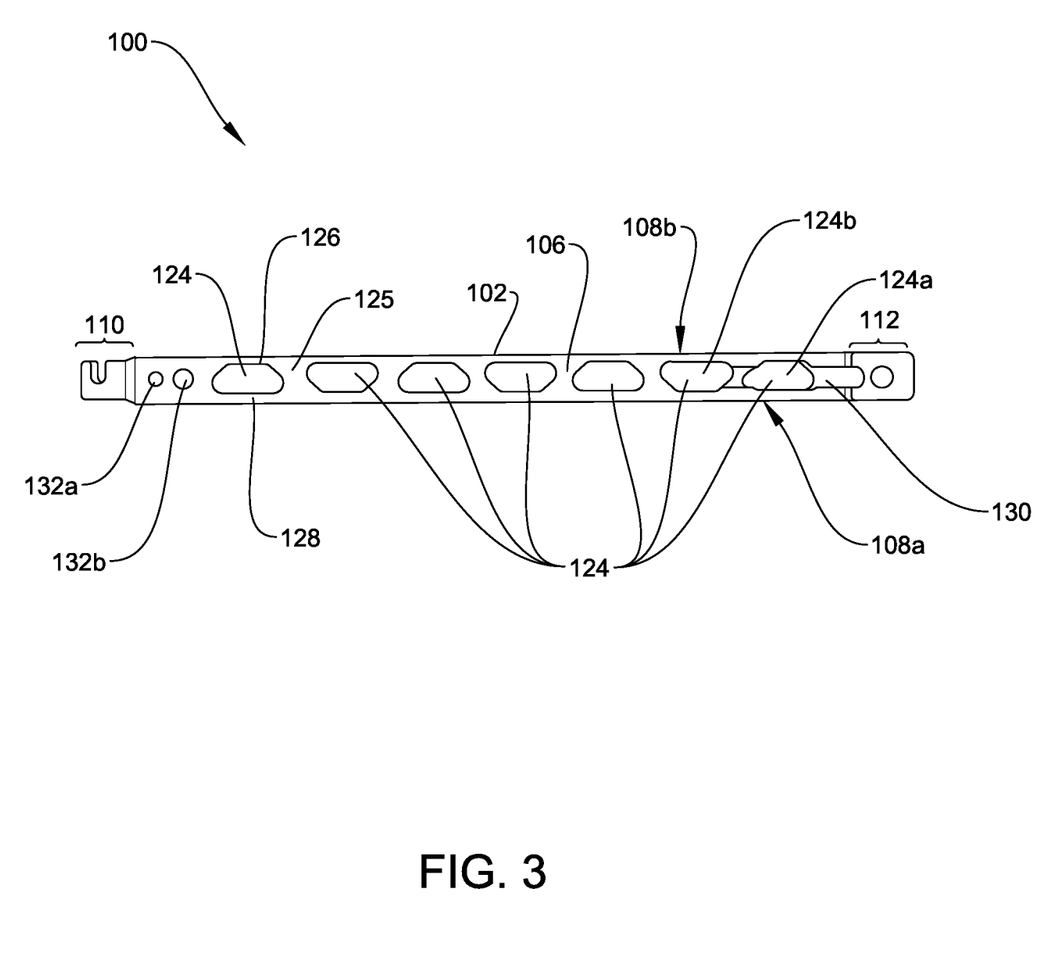
FIG. 3 is another side view of the tool of FIG. 1, with the spinal rod removed.
Figure 4:
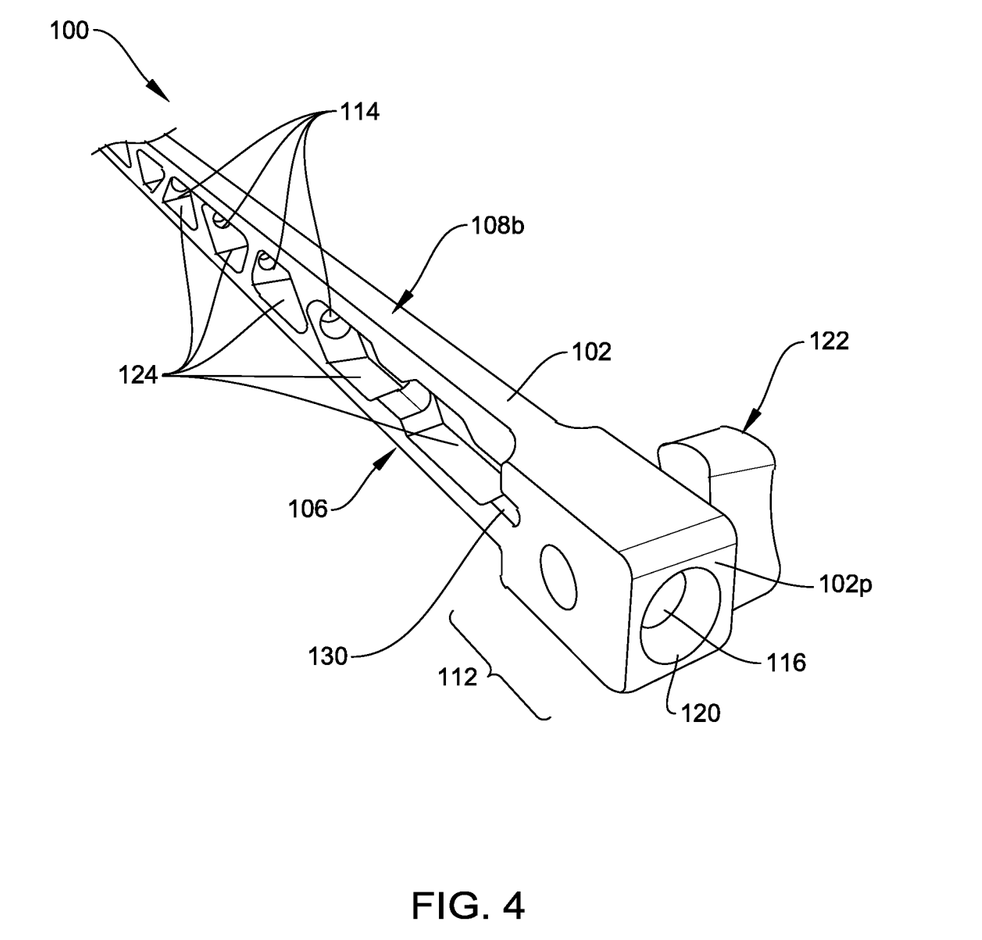
FIG. 4 is a perspective end view of the elongate shaft of the tool FIG. 1, with the spinal rod removed.
Figure 6:
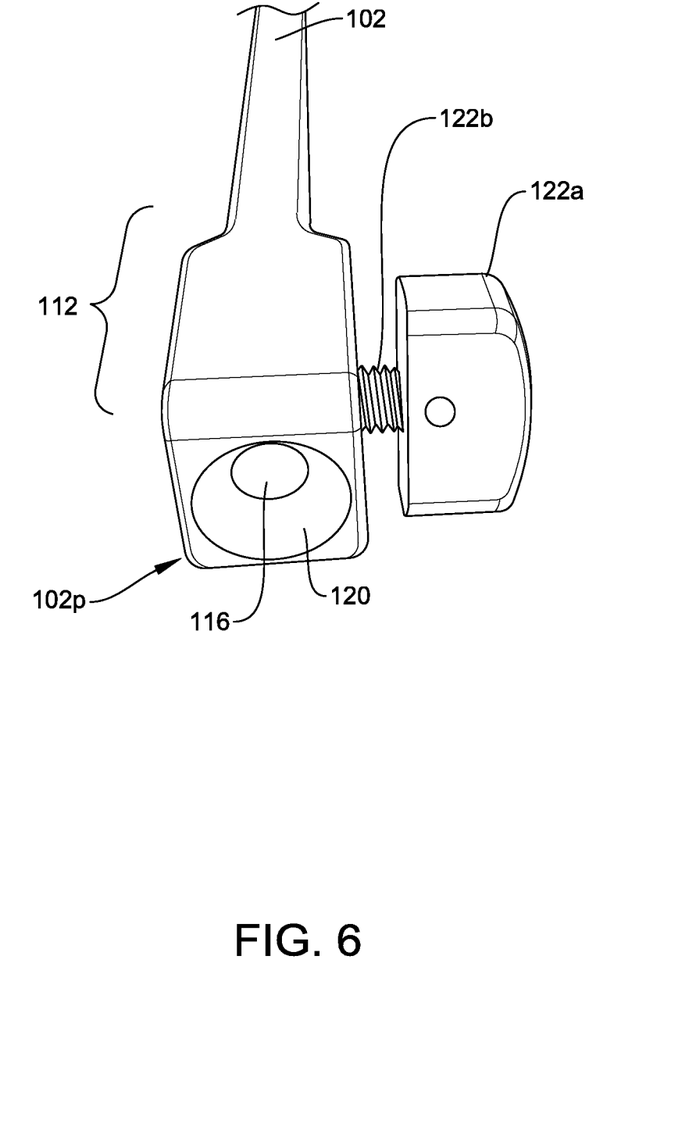
FIG. 6 is a perspective end view of a proximal portion of the elongate shaft of the tool FIG. 1, with the spinal rod removed.

As further shown in FIGS. 1-4, the elongate shaft 102 can include a lumen 114 configured to accommodate the spinal rod R. The lumen 114 can extend through the elongate shaft 102, from a proximal opening 116 at the proximal end 102p of the elongate shaft 102 and terminating proximal to the distal portion 110 of the elongate shaft 102. In other embodiments, the lumen 114 can extend through the entire length of the elongate shaft 102. The lumen 114 can have a variety of shapes and sizes, however in the illustrated embodiment the lumen 114 has a substantially circular cross-sectional shape and a diameter such that the lumen 114 can accommodate a cylindrical spinal rod having a complementary diameter therein. In order to facilitate insertion of a spinal rod R into the lumen 114, the proximal opening 116 can include a tapered region 120, as shown in FIGS. 4 and 6. In some implementations, the tapered region 120 can be configured to restrict a radius of curvature of the spinal rod R introduced into the spinal rod R during bending. Other geometries for the opening 116 are possible.

As further shown in FIGS. 2 and 3, the elongate shaft 102 can include a plurality of openings 124 spaced along the length thereof and extending entirely through the upper surface 104 and the lower surface 106. The plurality of openings 124 can intersect the lumen 114 such that a rod R extending through the lumen 114 will be disposed within and visible through the openings 124. The plurality of openings 124 can have a variety of shapes and sizes. In the illustrated embodiment, each of the plurality of openings 124 has a shape in the form of an isosceles trapezoid with rounded corners. In this embodiment, the shape of the plurality of openings 124 is configured to accommodate a locking mechanism 122 of a second spinal rod bending tool 100, as will be discussed in more detail below. In this arrangement, the spinal rod bending tool 100 can act as a wrench to facilitate unlocking of the locking mechanism 122 in the event it becomes difficult for a user to unlock it by hand.

The plurality of openings 124 can also have a variety of orientations. In some embodiments, with reference to FIG. 3, each of the plurality of openings 124 can have a short side 126 and a long side 128 extending substantially parallel to the side surfaces 108a, 108b. In the illustrated embodiment, the orientation of the plurality of openings 124 alternates between a first position where the short side 126 is oriented toward side surface 108a of the elongate shaft 102, and a second position where the long side 128 is oriented toward side surface 108a of the elongate shaft 102. As a result, the elongate shaft 102 has cross-bars 125 extending between each opening and between the side surfaces 108a, 108b to form a truss-like structure. An advantage of this orientation is that it can provide added structural rigidity to the tool 100. However, it is possible for the tool 100 to have other shapes and orientations for each of the plurality of openings 124. The plurality of openings 124 can also vary in number, based on the length of the tool 100 and the desired sizing of the openings 124. In the illustrated embodiment, the tool 100 has seven openings 124 spaced equidistant therealong.

Figure 1:
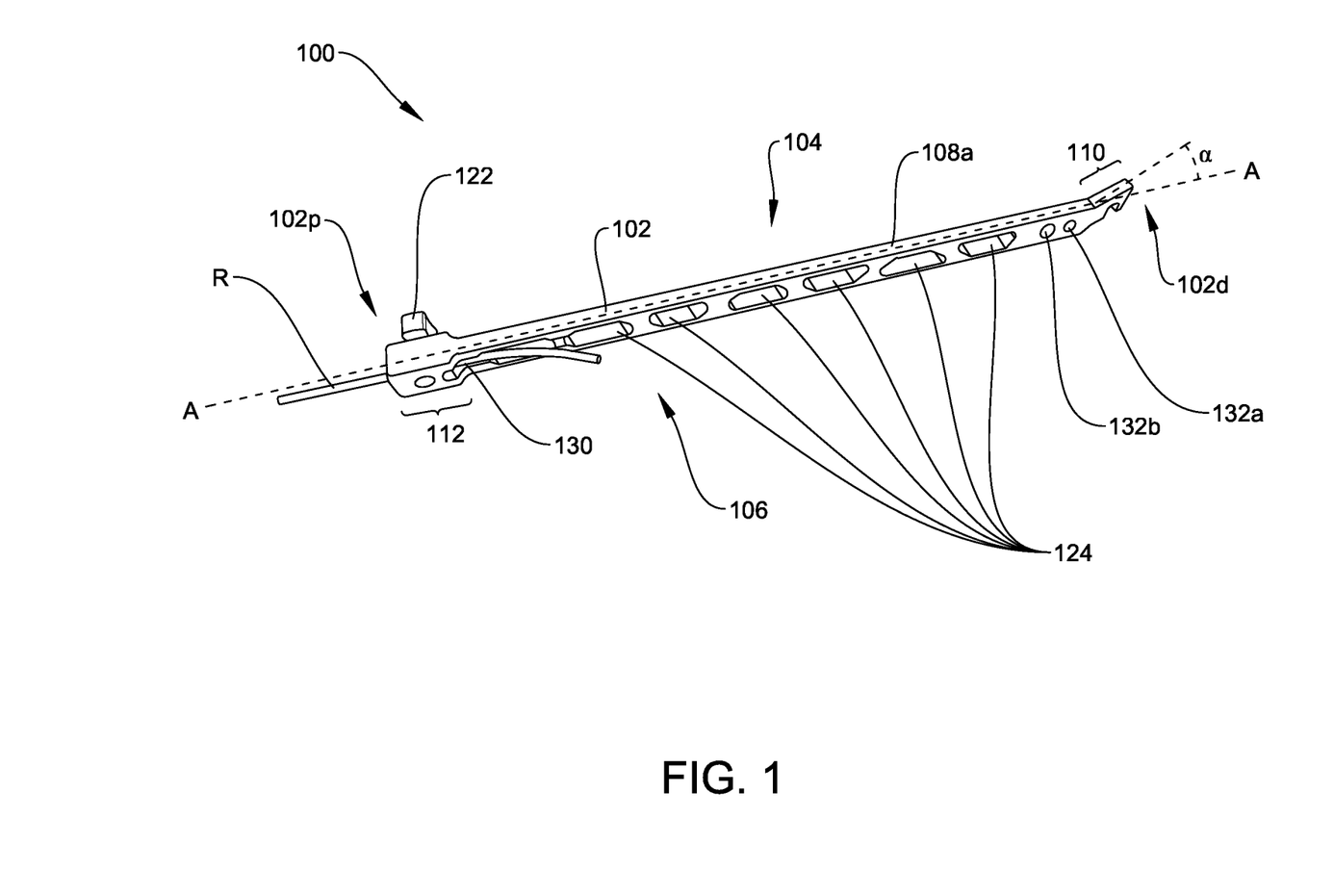
FIG. 1 is a perspective side view of one exemplary embodiment of a spinal rod bending tool having an elongate shaft, with a spinal rod inserted therein.

As further shown in FIGS. 1, 3, and 4, the elongate shaft 102 can include a groove or channel 130 formed in the lower surface 106 thereof and spaced apart from, but adjacent to the proximal opening 116. The channel 130 can be configured to accommodate a pre-bent spinal rod to permit the pre-bent spinal rod to extend laterally away from the lower surface 106 (as shown in FIG. 1). In the illustrated embodiment, the channel originates in the proximal portion 112 of the elongate shaft 102 and extends across a first opening 124a of the plurality of openings and into a second opening 124b of the plurality of openings. In this arrangement, the channel 130 connects the first and second of the plurality of openings 124a, 124b across the lower surface 106. The shape of the channel 130 can vary, but in the illustrated embodiment the channel 130 is generally hemi-cylindrical in shape for receiving a cylindrical rod R.

Figure 5:
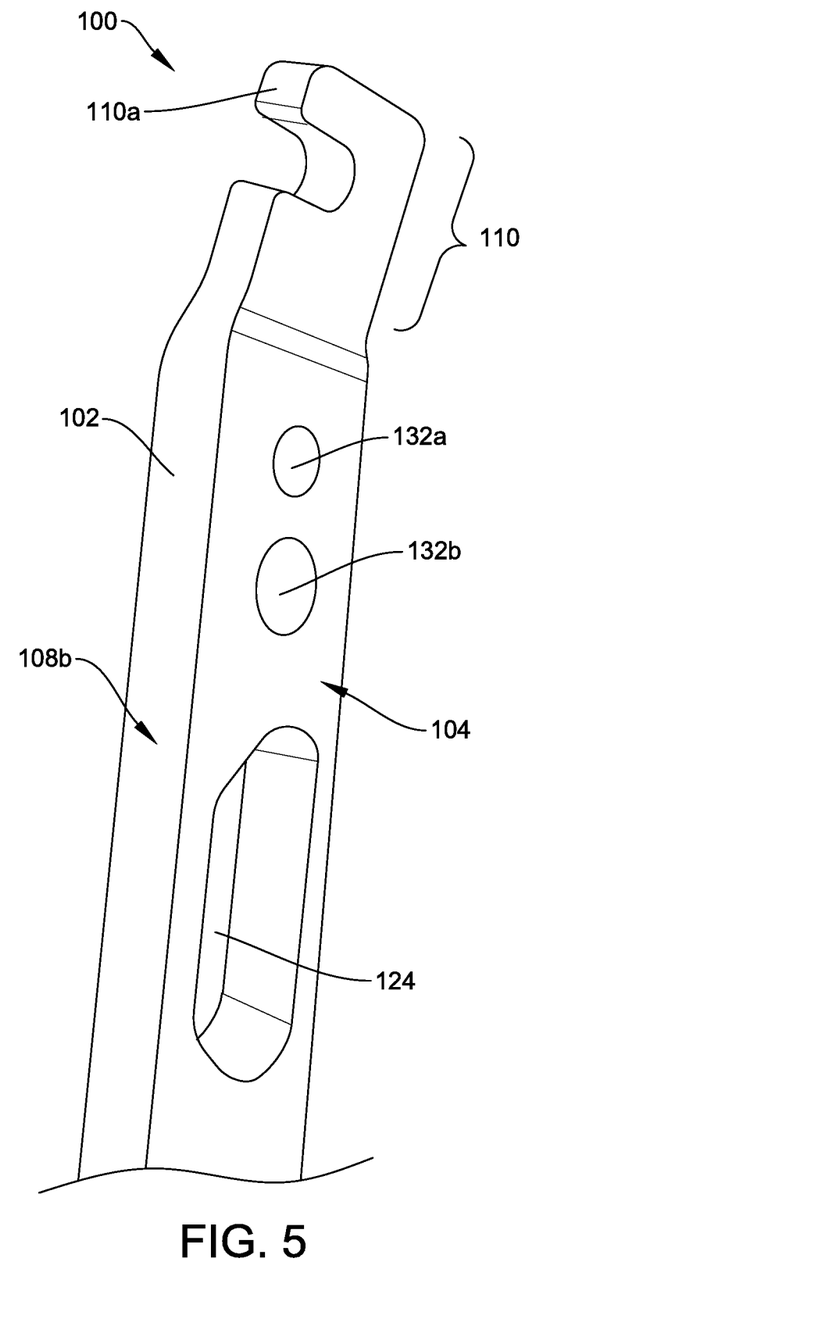
FIG. 5 is a perspective side view of a distal portion of the elongate shaft of the tool FIG. 1, with the spinal rod removed.

As further shown in FIG. 5, the elongate shaft 102 can include one or more distal thru-holes 132a, 132b formed therein adjacent and proximal to the distal portion 110 of the elongate shaft 102. The distal thru-holes 132a, 132b can extend entirely through the shaft 102 from the upper surface 104 to the lower surface 106. The distal thru-holes 132a, 132b can each be configured to receive a rod therethrough to facilitate further bending of the rod, as may be desired. Each thru-hole can have the same diameter, or can have differing diameters as shown to accommodate different sized rods.

As previously mentioned, the elongate shaft 102 can include a distal portion 110 which can be oriented at a transverse angle α to the longitudinal axis A of the elongate shaft, as shown in FIGS. 1 and 4. The angle α can be between 1 and 90 degrees, and more preferably is about 15 degrees. The distal portion can further include a hook 110a which is configured to engage a spinal rod along its length to further facilitate bending of the spinal rod. The hook 110a can have a variety of sizes and shapes, but in general the hook 110a can be in the form of a u-shaped recess extending into a side surface (e.g., side surface 108b) of the elongate shaft 102. A user can benefit from the hook 110a being mounted on the angled distal portion 110 of the elongate shaft, as the angled orientation of the hook 110a can provide additional leverage to a user when the shaft is being used to bend the spinal rod. For example, a user can engage two portions of a spinal rod with the hooks 110a on two tools 100, and can manipulate the tools relative to one another to bend a portion of the rod extending between the hooks 110a, 110b.

Figure 7:
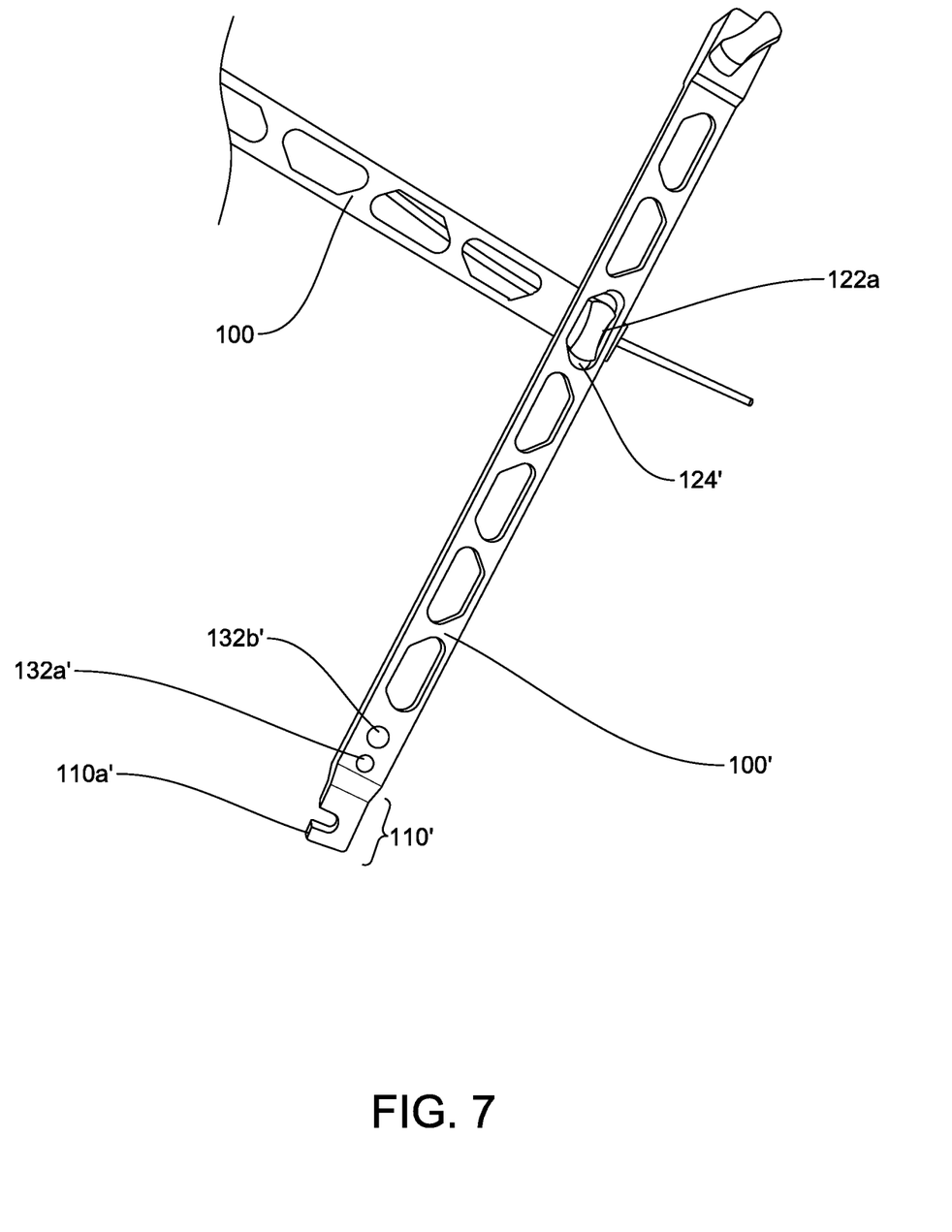
FIG. 7 is a perspective view of two tools 100 and 100' of the embodiment of FIG. 1, with one tool 100' being used to unlock a locking mechanism of the other tool 100.
Figure 8:
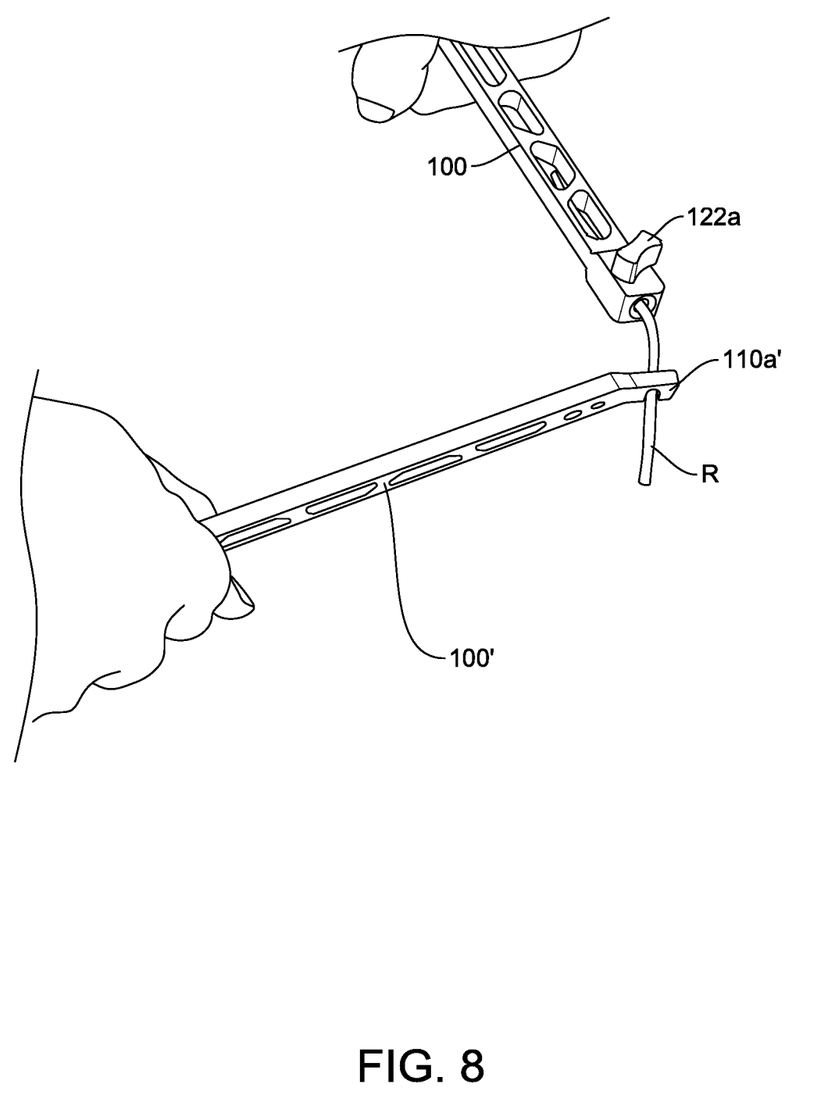
FIG. 8 is a perspective view of two tools 100 and 100' of the embodiment of FIG. 1, with a distal portion of one tool 100' being used to bend a rod inserted into a lumen of the other tool 100.
Figure 9:
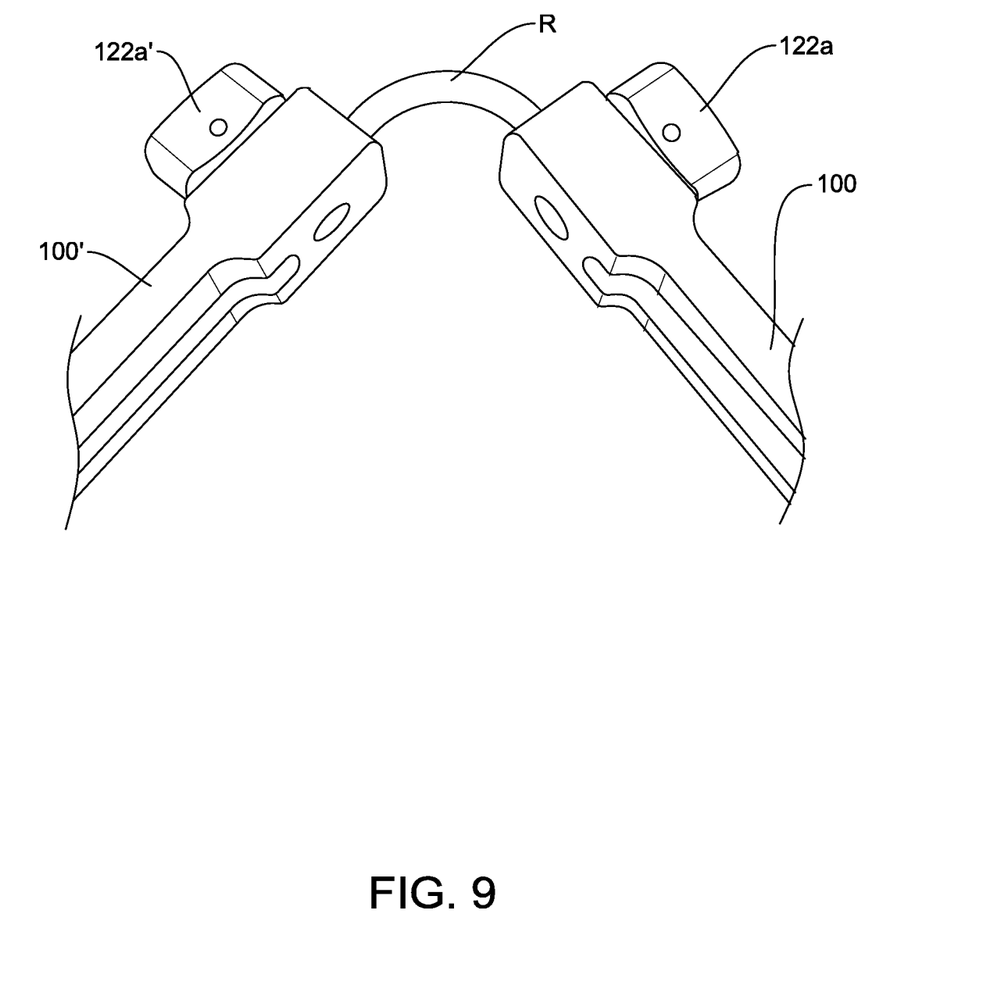
FIG. 9 is perspective view of two tools 100 and 100' of the embodiment of FIG. 1, with a proximal portion of each tool 100, 100' being used to bend a rod inserted into the lumen of each tool 100, 100'.

As previously mentioned, the elongate shaft 102 can, in some implementations, include a locking mechanism 122 coupled to the proximal portion 112 of the elongate shaft 102. The locking mechanism 122 can be configured to engage and retain a spinal rod in the lumen 114 to prevent sliding movement of the rod through the lumen. The locking mechanism 122 can have a variety of configurations, but in the illustrated embodiment, as best shown in FIG. 6, the locking mechanism 122 has a winged knob 122a with a set screw 122b extending therefrom and threadably coupled to a threaded locking mechanism thru-hole (not shown) formed in the proximal portion 112 of the elongate shaft 102. The threaded locking mechanism thru-hole extends from the upper surface of the proximal portion 112 to the lumen 112 extending through the proximal portion 112. The winged knob 122a is configured to be rotated to thread the set screw 122b with respect to the locking mechanism thru-hole. When a rod is inserted through the lumen 114, the set screw 122b will engage the rod and thereby longitudinally fix the rod within the lumen 114. The winged knob portion 122a can be rotated manually by hand if desired, or it can be inserted into one of the plurality of openings 124 on a second spinal rod bending tool 100, should a user require additional leverage to rotate the locking mechanism 122. This is illustrated in FIG. 7, which shows two spinal rod bending tools 100 and 100'. A user can insert the spinal rod R into the proximal opening of the lumen in the elongate shaft 102 of a first spinal rod bending tool 100 and can rotate the winged knob 122a of the locking mechanism to lock the spinal rod R in place. A user can use the hook 110a' on the distal portion 110' of the second spinal rod bending tool 100' or one of the distal thru-holes 132a', 132b' to grasp the spinal rod R. With the appropriate amount of force applied, the user can bend the rod to the desired position at a given location, as shown in FIG. 8. When the user desires to remove or reposition the bent spinal rod, the user can position the winged knob 122a of the locking mechanism 122 of the first spinal rod bending tool 100 within one of the plurality of openings 124' of the second spinal rod bending tool 100', as shown. The user can then rotate the second spinal rod bending tool 100' and thereby unlock the locking mechanism 122 on the first spinal rod bending tool 100, permitting the rod R to be removed from or repositioned within the lumen 114. The user can repeat this process as many times as desired, until the rod is bent into the desired shape for delivery to a spinal implant site. Since the tool 100 includes a channel (shown in FIG. 1) on the lower surface thereof that allows the rod R to extend the lumen 114 and extend laterally away from the elongate shaft 102, as shown in FIGS. 1 and 7, the user can advance the bent rod further into the lumen 114 in the tool 100 to bend additional portions of the rod. A user can also bend the spinal rod by using the proximal portion 112' of the second spinal rod bending tool 100', as shown in FIG. 9. In such an arrangement, while the spinal rod is inserted into the lumen 114 of the first spinal rod bending tool 100, the user can insert an opposed end of the spinal rod into the lumen (not shown) of the second spinal rod bending tool 100' and lock the end of the spinal rod in the lumen by rotating the winged knob 122a', which functions in the same manner as winged knob 122a. The user can then use both tools 100 and 100' to bend the rod to the desired position, as shown in FIG. 9.

The tools disclosed herein can be designed to be disposed of after a single use, or they can be designed to be used multiple times. In either case, however, the tool can be reconditioned for reuse after at least one use. Reconditioning can include any combination of the steps of disassembly of the tool, followed by cleaning or replacement of particular pieces, and subsequent reassembly. In particular, the tool can be disassembled, and any number of the particular pieces or parts of the tool can be selectively replaced or removed in any combination. Upon cleaning and/or replacement of particular parts, the tool can be reassembled for subsequent use either at a reconditioning facility, or by a surgical team immediately prior to a surgical procedure. Those skilled in the art will appreciate that reconditioning of a tool can utilize a variety of techniques for disassembly, cleaning/replacement, and reassembly. Use of such techniques, and the resulting reconditioned tool, are all within the scope of the present application.

Preferably, the tools and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A spinal rod bending tool, comprising:
   an elongate shaft extending along a longitudinal axis and having a substantially rectangular cross section, orthogonally oriented relative to the longitudinal axis, with upper and lower surfaces;
   a rod-receiving lumen extending at least partially through the elongate shaft along the longitudinal axis, the rod-receiving lumen having a proximal opening at a proximal end of the elongate shaft that is configured to receive a spinal rod therein;
   a plurality of openings spaced along the longitudinal axis and extending entirely through the upper and lower surfaces of the elongate shaft such that a user can grasp a rod extending through the rod-receiving lumen and positioned within one of the plurality of openings; and
   an extended opening formed in the lower surface of the elongate shaft adjacent to the proximal opening, the extended opening being configured to allow a pre-bent rod inserted through the proximal opening and into the rod-receiving lumen to extend laterally away from the lower surface.

2. The tool of claim 1, wherein the extended opening extends across and connects a first opening and a second opening of the plurality of openings.

3. The tool of claim 1, wherein the rod-receiving lumen terminates proximal to a distal end of the elongate shaft.

4. The tool of claim 1, wherein a distal portion of the elongate shaft is oriented at a transverse angle to the longitudinal axis of the elongate shaft.

5. The tool of claim 1, further comprising a locking feature at the proximal end of the elongate shaft, the locking feature being configured to engage and lock a rod extending through the rod-receiving lumen.

6. The tool of claim 1, wherein each of the plurality of openings has a shape in the form of an isosceles trapezoid.

7. The tool of claim 6, wherein each of the plurality of openings has a short side and a long side, and wherein the plurality of openings alternate between the short side and the long side being oriented toward a first side of the elongate shaft.

8. The tool of claim 1, wherein the upper and lower surfaces have a width that is greater than a height of opposed side surfaces extending between the upper and lower surfaces.

9. A rod bender tool, comprising:
   an elongate rectangular shaft having
      proximal end and distal ends defining a longitudinal axis,
      a substantially cylindrical lumen extending therethrough from the proximal end and terminating proximal to the distal end,
      a plurality of thru-holes spaced along the longitudinal axis, each thru-hole intersecting the substantially cylindrical lumen,
      an elongate channel formed in a lower surface of the elongate shaft, the elongate channel intersecting at least two of the thru-holes and intersecting the substantially cylindrical lumen.

10. The tool of claim 9, wherein the elongate rectangular shaft has upper and lower surfaces with the plurality of thru-holes extending through the upper and lower surfaces, and wherein the elongate channel is formed in a lower surface.

11. The tool of claim 9, wherein a distal portion of the elongate shaft is oriented at a transverse angle to the longitudinal axis of the elongate shaft.

12. The tool of claim 9, further comprising a locking feature at the proximal end of the elongate shaft, the locking feature being configured to engage and lock a rod extending through the substantially cylindrical lumen.

13. The tool of claim 9, wherein each of the plurality of openings has a shape in the form of an isosceles trapezoid.

14. The tool of claim 13, wherein each of the plurality of openings has a short side and a long side, and wherein the plurality of openings alternate between the short side and the long side being oriented toward a first side of the elongate shaft.

15. A method for bending a rod, comprising:
   inserting a pre-bent spinal rod into a lumen extending longitudinally through an elongate shaft of a rod bender tool such that a leading end of the rod extends through one of a plurality of openings formed in the elongate shaft and transversely oriented relative to the longitudinal axis of the elongate shaft, projects from a lower surface of the elongate shaft, and extends laterally away from the longitudinal axis of the elongate shaft; and grasping and manipulating a remaining trailing end of the pre-bent spinal rod extending from a proximal end of the elongate shaft to bend the remaining trailing end.

16. The method of claim 15, wherein at least a portion of the pre-bent spinal rod extends through a channel formed in the lower surface of the elongate shaft, the channel being in communication with first and second openings of the plurality of openings.

17. The method of claim 15, further comprising grasping a portion of the pre-bent spinal rod extending through one of the plurality of openings.

18. The method of claim 15, further comprising partially retracting the pre-bent spinal rod from the lumen, and repeating the step of grasping and manipulating theft remaining trailing end of the pre-bent spinal rod extending from the proximal end of the elongate shaft to bend the remaining trailing end.

19. The method of claim 15, further comprising, prior to grasping and manipulating, actuating a locking mechanism to lock the pre-bent spinal rod at a fixed position relative to the elongate shaft.

20. The method of claim 19, further comprising, after grasping and manipulating, releasing the locking mechanism by positioning the locking mechanism within one of a plurality of openings formed in a second rod bender tool, and rotating the tool to rotate the locking mechanism.

* * * * *